United States Patent [19]

Barberio

[11] 4,394,371

[45] Jul. 19, 1983

[54] DENTRIFRICE PREPARATION

[75] Inventor: Giacinto G. Barberio, Urmston, England

[73] Assignee: Colgate-Palmolive Company, New York, N.Y.

[21] Appl. No.: 366,260

[22] Filed: Apr. 7, 1982

[30] Foreign Application Priority Data

Apr. 7, 1981 [GB] United Kingdom .............. 81/10857

[51] Int. Cl.$^3$ .......................... A61K 7/16; A61K 7/18
[52] U.S. Cl. ........................................ 424/52; 424/57; 424/49; 206/524.1; 206/524.4; 206/524.5
[58] Field of Search .................................. 424/49–58; 206/524.1, 524.4, 524.5

[56] References Cited

U.S. PATENT DOCUMENTS

| | | | |
|---|---|---|---|
| 2,876,166 | 3/1959 | Nebergall | 424/52 |
| 3,269,814 | 8/1966 | Netherton et al. | 424/57 |
| 3,308,029 | 3/1967 | Saunders et al. | 424/57 |
| 3,662,060 | 5/1972 | Clippingdale et al. | 424/57 |
| 3,678,155 | 7/1972 | Clippingdale et al. | 424/52 |
| 3,699,220 | 10/1972 | Westrate et al. | 424/57 |
| 3,934,002 | 1/1976 | Habfele | 424/54 |
| 3,966,901 | 6/1976 | Cullum et al. | 424/52 |
| 4,193,988 | 3/1980 | Forward et al. | 424/52 |
| 4,259,316 | 3/1981 | Nakashima et al. | 424/52 |
| 4,305,928 | 12/1981 | Harvey | 424/52 |
| 4,335,102 | 6/1982 | Nakashima et al. | 424/52 |

FOREIGN PATENT DOCUMENTS

| | | | |
|---|---|---|---|
| 506291 | 6/1971 | Switzerland . | |
| 1005089 | 9/1965 | United Kingdom . | |
| 1408922 | 10/1975 | United Kingdom | 424/52 |
| 1547874 | 6/1979 | United Kingdom . | |

Primary Examiner—Shep K. Rose
Attorney, Agent, or Firm—Robert L. Stone; Murray M. Grill; Herbert S. Sylvester

[57] ABSTRACT

Preparations containing alkali metal monofluorophosphate anticaries material, alkaline earth metal orthophosphate polishing material and water soluble alkali metal trimetaphosphate are disclosed which can be used in unlined aluminium tubes by virtue of the presence of defined amounts of phytic acid.

4 Claims, No Drawings

DENTRIFRICE PREPARATION

This invention relates to a dentifrice preparation. More particularly it relates to a dentifrice preparation containing a water-soluble alkali metal monofluorophosphate, an alkaline earth metal orthophosphate polishing agent, an alkali metal trimetaphosphate and an additive to stabilize the dentifrice in an unlined aluminum tube.

Monofluorophosphate dentifrices which effectively provide anticaries amounts of fluoride and in which the polishing agent is principally an alkaline earth metal orthophosphate are well known; See for example British Pat. Nos. 1,005,089; 1,089,367; and 1,331,249. Improved anticariogenic effect was described for such dentifrices in British Pat. No. 1,275,816, through the addition of a trimetaphosphate, particularly sodium trimetaphosphate. Sodium trimetaphosphate was also described in a dentifrice containing sodium monofluorophosphate and silica xerogel abrasive in British Pat. No. 1,547,874.

The addition of the trimetaphosphate to the monofluorophosphate dentifrice containing alkaline earth metal orthophosphate polishing agent has, however, diminished compatibility of the dentifrice preparation with an unlined aluminum tube and made the use of an aluminum tube containing a protective inner lining advisable.

It is an object of this invention to provide a dentifrice preparation containing monofluorophosphate, alkaline earth metal orthophosphate polishing agent and a trimetaphosphate which is compatible with the aluminum surface of an aluminum dentifrice tube.

It is a further object of this invention to provide an aluminum dentifrice tube having therein a dentifrice preparation containing monofluorophosphate, alkaline earth metal orthosphosphate polishing agent and a trimetaphosphate which is compatible with the aluminium surface of the dentifrice tube.

In accordance with certain of its aspects this invention relates to a dentifrice preparation containing a dentifrice vehicle and dispersed therein a non-toxic anticaries amount of a water-soluble alkali metal monofluorophosphate, about 20-75% by weight of dentally acceptable alkaline earth metal orthophosphate polishing material, about 0.01-20% by weight of a water-soluble alkali metal trimetaphosphate and at least about 0.4% by weight of phytic acid. The phytic acid is a stabilizing additive to render the said dentifrice preparation compatible with an aluminium surface of a dentifrice tube.

The invention also extends to a dentifrice preparation containing a dentifrice vehicle and dispersed therein a non-toxic anticaries amount of a water-soluble alkali metal monofluorophosphate, 20-75% by weight of dentally acceptable alkaline earth metal orthosphosphate polishing material, 0.01-20% by weight of a water-soluble alkali metal trimetaphosphate and an amount of phytic acid effective to reduce attack by the dentifrice on the aluminium of an unlined aluminium tube.

The invention further extends to a dentifrice product comprising an unlined aluminium dentifrice tube containing a dentifrice preparation in accordance with the invention.

The water-soluble monofluorophosphate is preferably sodium monofluorophosphate. Sodium monofluorophosphate ($Na_2PO_3F$) is a water-soluble material which releases monofluorophosphate ions in water, and it may be mixed with the polishing material in any suitable amount. Such dental preparation is compatible with suitable amounts of conventional dentifrice constituents such as surface-active agents and gums, as described. The sodium monofluorophosphate as commercially available may vary considerably in purity. It may be used in any suitable purity provided that any impurities do not substantially adversely affect the desired properties. In general, the purity is desirably at least about 80%. For best results, it should be at least 85%, and preferably at least 90% by weight of sodium monofluorophosphate with the balance being primarily impurities or by-products of manufacture such as sodium fluoride and water-soluble sodium phosphate salt. Expressed in another way, the sodium monofluorophosphate should have a total fluoride content of above 12%, preferably above 12.7%; a content of not more than 1.5%, preferably not more than 1.2% of free sodium fluoride; and a sodium monofluorophosphate content of at least 12%, preferably 12.1%, all calculated as fluorine.

In addition to sodium monofluorophosphate, other monofluorophosphate salts which have sufficient water solubility for use in the instant invention include potassium monofluorophosphate. The term "monofluorophosphate" also includes monofluoropolyphosphates such as $Na_4P_3O_9F$, $K_4P_3O_9F$, $(NH_4)_4P_3O_9F$, $Na_3KP_3O_9F$, $(NH_4)_3\text{-}NaP_3O_9F$ and $Li_4P_3O_9F$.

The amount of monofluorophosphate in the dentifrice may be varied but should be an effective, non-toxic amount providing about 0.01-1% by weight of fluorine to the dentifrice. Thus, sodium monofluorophosphate is typically used in an amount of about 0.05-7.6% by weight. It is preferred that the sodium monofluorophosphate salt be no more than about 2%, and usually within the range of about 0.05% to about 1% by weight of the dentifrice. Alkaline earth metal orthophosphates may be employed in the hydrated or anhydrous form or as mixtures thereof. Dicalcium orthophosphate dihydrate, anhydrous dicalcium orthophosphate, dimagnesium orthophosphate trihydrate and dimagnesium orthophosphate heptahydrate may be used as the alkaline earth metal orthophosphate in accordance with the invention. Dicalcium orthophosphate dihydrate or mixtures thereof with anhydrous dicalcium phosphate are preferred. The alkaline earth metal orthophosphate may be considered as partially hydrated in a mixture of hydrated salts or hydrated and anhydrous salts in any suitable ratio resulting from a blend or formed in situ during manufacture.

An additional polishing agent may be employed with the orthophosphate insofar as tube compatibility is not substantially diminished by the inclusion of phytic acid in the dentifrice preparation.

As mentioned before, trimetaphosphate salt has been disclosed in British Pat. No. 1,275,816 as an improved anticaries additive to a dentifrice containing a monofluorophosphate and an orthophosphate polishing agent, water soluble alkali metal trimetaphosphate with a halogenated trifluoromethylsalicylanilide in Swiss Pat. No. 506,292 and in British Pat. No. 1,547,874 in which sodium trimetaphosphate is disclosed in combination with a silica xerogel. Such dentifrices too may optionally contain a monofluorophosphate and a orthophosphate polishing agent. The water-soluble trimetaphosphate can contribute improved anticaries effect particularly when present in an amount of about 0.01-20% by weight, preferably about 0.2-15% and most preferably about 0.5–5%. When it has been present, it has been advisable to employ an aluminium dentifrice tube containing a protective inner lining, since it diminishes the compatibility of the dentifrice preparations with an aluminium surface.

In the present invention it has been found that the presence of phytic acid in amount of at least about 1% by weight, overcomes the incompatibility discussed above and renders the dentifrice preparations compatible with an unprotected aluminium surface.

Phytic acid (inositol hexaphosphoric acid, $C_6H_6O_6(H_2PO_3)_6$) has ben previously disclosed as a dentifrice component, but its use with monofluorophosphate, alkaline earth metal orthophosphate polishing agent and trimetaphosphate to stabilize a dentifrice preparation containing these components for use in unlined aluminium tube has hitherto not been known. Prior disclosures of phytic acid in dentifrices are: U.S. Pat. No. 3,934,002 wherein phytic acid is disclosed to remove stain caused by a cationic bisbiguanide antiplaque agent; German Patent Publication No. 2,918,134 wherein phytic acid is disclosed as an antifade additive for a visually clear dentifrice; French Patent Publication No. 2,170,018 wherein phytic acid is disclosed as a component of a portion of a remineralising dentifrice; and British Pat. No. 1,384,375 wherein phytic acid is disclosed as a component of a dentifrice containing calcium carbonate polishing agent.

Amounts of phytic acid in the dentifrice preparation of the invention of less than about 0.4% by weight have not been observed to achieve the desired compatibility with an aluminum surface. Larger amounts of phytic acid may be used, although the pH of the dentifrice preparation should desirably remain typically about 5–9. If desired, the pH can be further adjusted with acidic or basic buffering agent. Typically about 0.4–10% by weight of phytic acid can be effectively used, preferably about 0.4–2% by weight. It is understood that pharmaceutically and cosmetically acceptable salts of phytic acid (e.g. sodium, or calcium salts) may be used by pre-formation or forming in-situ in the dentifrice preparation; these are included in the term "phytic acid".

In dental cream or toothpaste dentifrice formulations, the liquids and solids should necessarily be proportioned to form a creamy mass of desired consistency which for example is extrudable from a collapsible aluminium tube. In general, the liquids in the dental cream will comprise chiefly water, glycerine, sorbitol, polyethylene glycol, or propylene glycol 400, including suitable mixtures thereof. It is advantageous usually to use a mixture of both water, and a humectant such as glycerine, or sorbitol or mixtures thereof. The total liquid content will generally be about 20–75% by weight of the formulation. It is preferred to use also a gelling agent in dental creams such as the natural and synthetic gum-like materials, e.g. Irish Moss, gum tragacanth, sodium carboxymethylcellulose, polyvinylpyrrolidone, or starch. Irish Moss and sodium carboxymethylcellulose, are compatible particularly and are preferred gelling agents. The gum content is usually in an amount up to about 10% and preferably about 0.5–5% by weight of the formulation. Fillers such as pyrogenic silica and silica aerogel may also be used, typically in amount up to about 10% by weight to supplement the gelling agent.

Any suitable surface active or detersive material may be included in the dentifrice preparation. Such compatible materials are desirable to provide additional detersive, foaming and anti-bacterial properties depending upon the specific type of surface active material and are selected accordingly. These detergents are usually water-soluble organic compounds, and may be anionic, non-ionic or cationic in structure. It is preferred to use the water-soluble salts of higher fatty acid monoglyceride monosulphate detergents (e.g. sodium coconut fatty acid monoglyceride monosulphate), higher alkyl sulphates (e.g. sodium lauryl sulphate), alkyl aryl sulphonates (e.g. sodium dodecyl benzene sulphonate) or higher fatty acid esters of 1,2-dihydroxy propane sulphonate (e.g. sodium coconut fatty acid ester of 1,2-dihydroxy propane sulphonate).

The various active materials may be used in any suitable amount, generally from about 0.05 to about 10% by weight, and preferably from about 0.5 to 5% by weight of the dentifrice composition.

It is a further embodiment of the present invention to use the substantially saturated higher aliphatic amino carboxylic acid compounds, such as those having 12 to 16 carbon atoms in the acyl radical, and as more particularly described in U.S. Pat. No. 2,689,170, issued Sept. 14, 1954. The amino acid portion is derived generally from the lower aliphatic saturated monoaminocarboxylic acids having about 2 to 6 carbon atoms, usually the monocarboxylic acid compounds. Suitable compounds are the fatty acid amides of glycine, sarcosine, alanine, 3-amino propanoic acid and valine having about 12 to 16 carbon atoms in the acyl group. It is preferred to use the N-lauroyl, myristoyl and palmitoyl sarcoside compounds however for optimum effects.

The amide compounds may be employed in the form of the free acid or preferably as the water-soluble salts thereof, such as the alkali metal, ammonium, amine and alkylolamine salts. Specific examples thereof are sodium and potassium N-lauroyl, myristoyl and palmitoyl, ammonium and ethanolamine N-lauroyl sarcosides and N-lauroyl sarcosine, and sodium N-lauroyl glycide and alanide. For convenience herein, reference to "amino carboxylic acid compound", "sarcoside", and the like refers to such compounds having a free carboxylic group or the water-soluble carboxylate salts.

Such materials are utilized in pure or substantially pure form. They should be as free as practicable from soap or similar higher fatty acid material which tends to reduce the activity of these compounds. In usual practice, the amount of such fatty acid material is less than 15% by weight of the amide and insufficient to substantially adversely affect it, and preferably less than about 10% by weight of the said amide material.

A minor amount of hydrated aluminium oxide may be incorporated in the dentifrice preparation. More particularly, a dental cream having improved physical properties may be prepared from a mixture of the dicalcium orthophosphate dihydrate suspended in a gel comprising water, humectant and gelling agent, with monofluorophosphate compound and organic non-soap synthetic detergent, and preferably a minor amount of hydrated aluminium oxide. These dental creams exhibit a superior degree of cosmetic properties and physical stability to aging for long periods of time. The aluminium oxide acts as a stabilizing and modifying agent so as to eliminate or inhibit any tendency for separation or "bleeding" of the dental cream in the collapsible tube.

Suitable examples of hydrated aluminium oxide which may be employed are the forms known as alpha and beta aluminium oxide trihydrate and mixtures thereof. It is used usually in the form of fine particles of any desired particle size in the manufacture of the dental cream. It has been found that amounts of hydrated aluminium oxide of from about 0.25 to about 10% by weight are most desirable.

There may be employed also various calcium and magnesium ion suppression agents for adjustment of physical properties of the compositions. Suitable agents are the water-soluble inorganic polyphosphate salts, such as tetrasodium pyrophosphate or disodium diacid, pyrophosphate, with the partially neutralized or acid polyphosphates preferred. Other suitable agents are the alkali metal, preferably sodium, salts of citric acid. In general, such compounds will be a minor amount or proportion of the formulation. The precise amount will vary depending upon the specific formulation, such as the physical characteristics of the dental cream, but will usually be from about 0.1% to about 3% by weight.

Various other materials may be incorporated in the dentifrice preparations of this invention. Examples thereof are colouring or whitening agents or dyestuffs, preservatives, silicones, chlorophyll compounds, ammoniated materials such as urea, diammoniumphosphate and mixtures thereof, and other constituents. Adjuvants may be incorporated in the compositions of the present invention in amounts which do not substantially adversely affect the proportions and characteristics desired and are selected and used in proper amounts depending upon the particular type of preparation involved.

Antibacterial agents may also be employed in the dentifrice of the present invention in an amount of about 0.01–5% by weight. Typical antibacterial agents include $N^1$-(4-chlorobenzyl)-$N^5$-(2,4-dichlorobenzyl) biguanide;
p-chlorophenyl biguanide;
4-chlorobenzhydryl biguanide;
4-chlorobenzhydrylguanylurea;
N-3-lauroxylpropyl-$N^5$-p-chlorobenzylbiguanide;
1,6-di-chlorophenylbiguanidohexane;
1-(lauryldimethylammonium)-8-(p-chlorobenzyldimethylammonium) octane dichloride;
5,6-chloro-2-guanidinobenzimidazole;
$N^1$-p-chlorophenyl-$N^5$-laurylbiguanide;
5-amino-1,3-bis (2-ethylhexyl)-5-methylhexahydro pyrimidine;
and their non-toxic acid addition salts.

Suitable flavouring or sweetening sialagogues may be employed in formulating a flavour for the preparation of the present invention. Examples of suitable flavouring constituents include the flavouring oils, e.g. oils of spearmint, peppermint, wintergreen, sassafrass, clove, sage, eucalyptus, marjoram, cinnamon, lemon and orange, as well as methylsalicylate. Suitable sweetening agents include sucrose, lactose, maltose, sorbitol, sodium cyclamate and sodium saccharine. Suitably, the flavour and sweetening agent may together comprise from about 0.01 to 5% by weight or more of the compositions of the present invention.

The invention may be put into practice in various ways and a number of specific embodiments will be described to illustrate the invention with reference to the following specific examples. The compositions are prepared in the usual manner and all amounts of the various ingredients are by weight unless otherwise specified.

EXAMPLES 1A, B and C

Three toothpaste dentifrice preparations listed below were prepared by blending the gelling agent with the humectant and adding thereto monofluorophosphate, orthophosphate, trimetaphosphate and phytic acid. The toothpastes were then deaerated and each filled into a number of capped unlined aluminium tubes which were then sealed by crimping the bottom of the tube. The dentifrices thus prepared are as follows:

| Ingredient | Composition (Parts by Weight) | | |
| --- | --- | --- | --- |
| | A | B | C |
| Dicalcium orthophosphate dihydrate | 35.0 | 35.0 | 35.0 |
| Sodium monofluorophosphate | 0.9 | 0.9 | 0.9 |
| Sodium trimetaphosphate | 2.0 | 2.0 | 2.0 |
| Phytic Acid (40% solution) | — | 0.5 | 1.0 |
| Glycerine | 7.0 | 7.0 | 7.0 |
| Sorbitol (70% solution) | 16.0 | 16.0 | 16.0 |
| Sodium carboxymethyl cellulose | 1.5 | 1.5 | 1.5 |
| Silica aerogel | 2.0 | 2.0 | 2.0 |
| Sodium saccharin | 0.2 | 0.2 | 0.2 |
| Sodium lauryl sulphate | 2.0 | 2.0 | 2.0 |
| Flavour | 1.0 | 1.0 | 1.0 |
| Water | Q.S. to 100.0 in each example | | |

Columns A and B are comparison Examples 1A and 1B, column C is in accordance with the invention, Example 1C.

Samples were tested at two different temperatures; some were stored for 3 months in an oven at 43° C. and others for 6 months at room temperature. The tubes containing toothpastes A and B were swollen and gassed in both tests, evidencing incompatibility of the toothpaste with the unlined aluminium tube. The tubes containing Toothpaste C remained satisfactory both in the test for 3 months at 43° C. and in the test for 6 months at room temperature, showing that the presence of phytic acid in an amount of 0.4 parts per 100 parts (that is 40% of 1 part per 100 parts) had stabilized the toothpaste in the tube.

EXAMPLE 2

Similar compatibility with an unlined aluminium tube was exhibited when the 35.0 parts of dicalcium orthophosphate dihydrate in toothpaste C of Example 1 were replaced by 35.0 parts of dimagnesium orthophosphate trihydrate.

EXAMPLE 3

Similar compatibility with an unlined aluminium tube was exhibited when 17.5 parts of the dicalcium orthophosphate dihydrate in toothpaste C of Example 1 were replaced by 17.5 parts anhydrous dicalcium orthophosphate.

I claim:

1. A dentifrice preparation in an unlined aluminium tube containing a dentifrice vehicle and dispersed therein a non-toxic anticaries amount of a water-soluble alkali metal monofluorophosphate, 20–75% by weight of dentally acceptable alkaline earth metal orthophosphate polishing material, 0.01–20% by weight of a water-soluble sodium trimetaphosphate and an amount of at least 0.4% by weight phytic acid effective to reduce attack by the dentifrice on the aluminium of an unlined aluminium tube.

2. A dentifrice preparation containing a dentifrice vehicle and dispersed therein a non-toxic anticaries amount of a water-soluble alkali metal monofluorophosphate, 20–75% by weight of dentally acceptable alkaline earth metal orthophosphate polishing material, 0.01–20% by weight of a water-soluble alkali metal trimetaphosphate and at least 0.4% by weight of phytic acid.

3. A dentifrice preparation as claimed in claim 2 which contains 0.05–1% by weight of sodium monofluorophosphate, 25–60% by weight of dicalcium orthophosphate, 0.5–5% by weight of sodium trimetaphosphate and 0.4–10% by weight of phytic acid.

4. A dentifrice preparation as claimed in claim 3 in which the said dicalcium orthophosphate is dicalcium orthophosphate dihydrate.

* * * * *